Feb. 2, 1971 G. MERRILL Plant Pat. 3,024
PEACH TREE
Filed Feb. 6, 1969
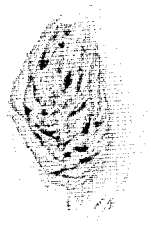
GRANT MERRILL
INVENTOR
Virgil L. Gerard
ATTORNEY United States Patent Office Plant Pat. 3,024
Patented Feb. 2, 1971

3,024

PEACH TREE

Grant Merrill, 416 N. Anderson Road,
Exeter, Calif. 93221

Filed Feb. 6, 1969, Ser. No. 797,286
Int. Cl. A01h 5/03
U.S. Cl. Plt.—43 1 Claim The present invention relates to a peach tree and more particularly to a new and distinct variety thereof broadly characterized by its heavy yields of fruit which is highly colored with red covering approximately half of its skin surface and has flesh that is free from the stone, has a buttery texture, is clear yellow in color with very little red except bright red near the stone, and when frozen, has high flavor, making it an excellent fruit for commercial freezing.

The instant variety is most nearly like Mardigras 2 (U.S. plant patent applied for, Ser. No. 730,688, now Plant Pat. No. 2,966) but is an improvement thereon in that it ripens three to five days earlier and has flesh which is more buttery, and has less red and a higher flavor, making it better for commercial freezing purposes.

I originated the present variety on a farm at Red Bluff, Tehama County, Calif., formerly owned by me, by crossing the J. H. Hale variety of peach (unpatented) with an open pollinated, third generation selection of a cross of J. H. Hale with Levi Cling (unpatented). It can be expressed as J. H. Hale × (J. H. Hale × Levi Cling F3). The resulting variety was then asexually reproduced and the characteristics of the reproduced tree and fruit were exactly the same.

The accompanying drawing is an oil painting of a characteristic fruit of the subject variety including a showing of the fruit divided on its suture plane to reveal flesh coloration and stone characteristics.

Referring more specifically to the pomological characteristics of this new and distinct variety of peach tree, the following has been observed under the ecological conditions prevailing at Exeter, Tulare County, Calif., and is an outline description thereof. All major color plate identifications are by reference to Maerz and Paul Dictionary of Color, 1st ed.

TREE

General: large, and medium spreading.
Productivity: very productive and a regular bearer.
Trunk: medium stocky, shaggy, gray in color.
Branches: gray in color and shaggy on older limbs; brown and smoother on younger branches; lenticels, numerous and medium size.

LEAVES (Selected from midportion of vigorous terminal shoots)

Size: medium thick, lanceolate, tip, accuminate.
Color: upper surface dark green; lower surface, lighter and more yellowish green; veins on underside, yellow green.
Class (Meador & Blake: Proceedings of the American Society for Horticultural Science, vol. 37, p. 203): large leaves mostly class 3; small leaves mostly class 2.
Markings: margins, glandular crenate; petiole, medium size; glands, reniform, and at base of leaf and on petiole, yellow to brown in color; at base of leaf on young leaves, dropping off early.

FLOWERS

Buds: medium size, plump, free, pubescent.
Season: medium late like Scarlet Lady (U.S. Plant Pat. No. 1,785.
Shape: small, non-showy.
Color: salmon pink.
Pollen: moderate in amount.

FRUIT

Maturity (when described): firm for nearby market or for freezing commercially.
Size: large and variable; diameter, axially 2⅜ to 3⅛ inches, transverse in suture plane 2½ to 3¼ inches, right angle to suture plane 2½ to 3¼ inches.
Form: generally globose to cordate in less ripe fruit; base retuse; apex generally rounded to mucronate; pistil point apical.
Suture: distinct, shallow, extends from base to near apex but is discontinuous adjacent apex; has slight depression beyond pistil point.
Ventral surface: slightly lipped in most, on both sides.
Dorsal side: rounded.
Cavity: flaring; generally elongated in suture plane, with suture showing on both sides, ¼ to ½ inch deep, 1⅛ to 1⅜ inches in breadth; markings, same yellow as on skin with red blush where exposed to the sun.
Stem: medium size.
Skin: medium thick, medium tough, tenacious to flesh, sweet, no tendency to crack; pubescence moderate to scant; color, undercolor yellow 9–K–7 with red over about half of the surface from light red 2–J–10 to dark red 6–L–6.
Flesh: color, yellow (generally 9–K–5) with red (generally 5–L–6) near stone and occasionally in flesh in firm ripe fruit with more red in soft ripe fruit; amygdalin, moderate; juice, moderate; texture, meaty when fresh, buttery when frozen; fibers, few and fine; ripens evently; flavor, mild vinuous; aroma, distinct; eating quality, excellent.

STONE

General: free from flesh.
Shape: obovate, tip, accuminate; base, straight to oblique; apex, accuminate and longer than most peaches; sides, equal to unequal; hilum, oval; surface, irregularly furrowed, mostly toward apex; pitted, generally toward base; pits generally elongated; fewer than most peaches; ventral edge thick with many small grooves extending full length of stone; dorsal edge with groove extending three-fourths the way from base toward apex in most.
Color (when fresh): light brown 14–J–10 to dark brown 48–L–12, but lighter in color when dried.

USE

Generally: for market and for commercial freezing, keeping quality good, shipping quality good.

Although the new variety of peach tree posses the described characteristics under the ecological conditions prevailing in Exeter, Tulare County, Calif., having been first observed near Red Bluff, Tehama County, Calif., it is to be understood that variations of the usual magnitude in characteristics incident to the growing conditions, fertilization, pruning and pest control is to be expected.

Having thus described and illustrated my new variety of peach tree, what is claimed is:

1. A new and distinct variety of peach substantially as illustrated and described, which is characterized by a very productive tree, bearing fruit which has a highly colored skin with red covering about half of the surface, and flesh which is buttery, completely free from the stone, clear yellow in color with very little red except bright red near the stone, and has a high flavor which carries into the frozen product when frozen; and which most nearly resembles Mardigras 2 (U.S. Plant Patent applied for, Ser. No. 730,688, now Plant Pat. No. 2,966) but is an improvement thereon in that the fruit ripens a few days earlier, has less red in the flesh, a higher flavor, and a texture that is more buttery when frozen.

No references cited.

ROBERT E. BAGWILL, Primary Examiner

UNITED STATES PATENT OFFICE

CERTIFICATE OF CORRECTION

Patent No. Plant Patent No. 3024 Dated February 2, 1971

Inventor(s) Grant Merrill

It is certified that error appears in the above-identified patent and that said Letters Patent are hereby corrected as shown below:

Column 1, line 20, and Column 3, line 6, "2966)", each occurrence, should read -- 2965) --.

Signed and sealed this 16th day of May 1972.

(SEAL)
Attest:

EDWARD M.FLETCHER,JR.
Attesting Officer

ROBERT GOTTSCHALK
Commissioner of Patents